(12) United States Patent
Eckert

(10) Patent No.: US 10,279,124 B2
(45) Date of Patent: May 7, 2019

(54) EXPANDING NEEDLE DEVICE AND METHOD OF EXPANSION FOR THE TRANSFER OF FLUIDS

(71) Applicant: Aesynt Incorporated, Cranberry Township, PA (US)

(72) Inventor: Robert Eckert, Eighty Four, PA (US)

(73) Assignee: Aesynt Incorporated, Cranberry Township, PA (US)

( * ) Notice: Subject to any disclaimer, the term of this patent is extended or adjusted under 35 U.S.C. 154(b) by 853 days.

(21) Appl. No.: 14/602,711

(22) Filed: Jan. 22, 2015

(65) Prior Publication Data

US 2016/0213399 A1 Jul. 28, 2016

(51) Int. Cl.
*A61M 5/32* (2006.01)
*A61M 5/178* (2006.01)

(52) U.S. Cl.
CPC .......... *A61M 5/329* (2013.01); *A61M 5/1782* (2013.01); *A61M 2205/195* (2013.01); *A61M 2205/368* (2013.01); *A61M 2209/00* (2013.01); *A61M 2209/045* (2013.01)

(58) Field of Classification Search
CPC .. A61M 2025/0024; A61M 2025/0025; A61M 5/34; A61M 5/346; A61M 2205/195; A61M 2205/368; A61M 5/329; A61M 2209/00; A61M 2209/045; A61M 5/1782; A61B 17/3439
See application file for complete search history.

(56) References Cited

U.S. PATENT DOCUMENTS

| 4,411,655 A | * | 10/1983 | Schreck ............ A61M 25/0662 |
| | | | 285/381.2 |
| 4,740,207 A | | 4/1988 | Kreamer |
| 4,877,030 A | | 10/1989 | Beck et al. |
| 4,950,258 A | | 8/1990 | Kawai et al. |
| 4,969,890 A | | 11/1990 | Sugita et al. |
| 5,007,926 A | | 4/1991 | Derbyshire |
| 5,059,211 A | | 10/1991 | Stack et al. |
| 5,078,726 A | | 1/1992 | Kreamer |
| 5,100,429 A | | 3/1992 | Sinofsky et al. |
| 5,108,416 A | | 4/1992 | Ryan et al. |

(Continued)

FOREIGN PATENT DOCUMENTS

EP 0382014 A1 8/1990
WO 2005089433 A2 9/2005

*Primary Examiner* — Brandy S Lee
(74) *Attorney, Agent, or Firm* — The Webb Law Firm

(57) ABSTRACT

An expanding needle is provided that includes a tubular body having a proximal end, a needle-tipped distal end, and a lumen extending therebetween. The expanding needle also includes a longitudinal seam formed on the tubular body. The tubular body is configured to uncurl radially, along the longitudinal seam, thereby transitioning the tubular body from a contracted state to an expanded state to increase an inner diameter of the lumen. In certain embodiments, the tubular body is formed by, for example, a continuous flexible sheet rolled in a lengthwise direction. In that case, the longitudinal seam is defined by a portion of a side of the flexible sheet overlapping an opposing side of the flexible sheet. An expanding needle device, including an expanding needle seated to a needle hub, and a method of increasing an inner diameter of an expanding needle are also provided herein.

23 Claims, 6 Drawing Sheets

(56) References Cited

U.S. PATENT DOCUMENTS

| | | | |
|---|---|---|---|
| 5,139,511 A * | 8/1992 | Gill | A61B 17/3439 |
| | | | 600/208 |
| 5,211,654 A | 5/1993 | Kaltenbach | |
| 5,957,862 A | 9/1999 | Lu et al. | |
| 6,127,597 A | 10/2000 | Beyar et al. | |
| 7,435,240 B2 | 10/2008 | Barkhahn et al. | |
| 7,803,142 B2 | 9/2010 | Longson et al. | |
| 8,062,437 B2 | 11/2011 | Cichocki et al. | |
| 8,251,963 B2 | 8/2012 | Chin et al. | |
| 8,663,168 B2 | 3/2014 | Chin et al. | |
| 2001/0012950 A1 * | 8/2001 | Nishtala | A61M 25/0662 |
| | | | 606/198 |
| 2004/0064107 A1 | 4/2004 | Lo | |
| 2006/0212062 A1 | 9/2006 | Farascioni | |
| 2007/0060927 A1 | 3/2007 | Longson et al. | |
| 2011/0021994 A1 * | 1/2011 | Anderson | A61B 17/3415 |
| | | | 604/164.01 |
| 2013/0197452 A1 | 8/2013 | Tachikawa et al. | |
| 2014/0142509 A1 | 5/2014 | Bonutti et al. | |
| 2014/0148767 A1 | 5/2014 | Chin et al. | |

* cited by examiner

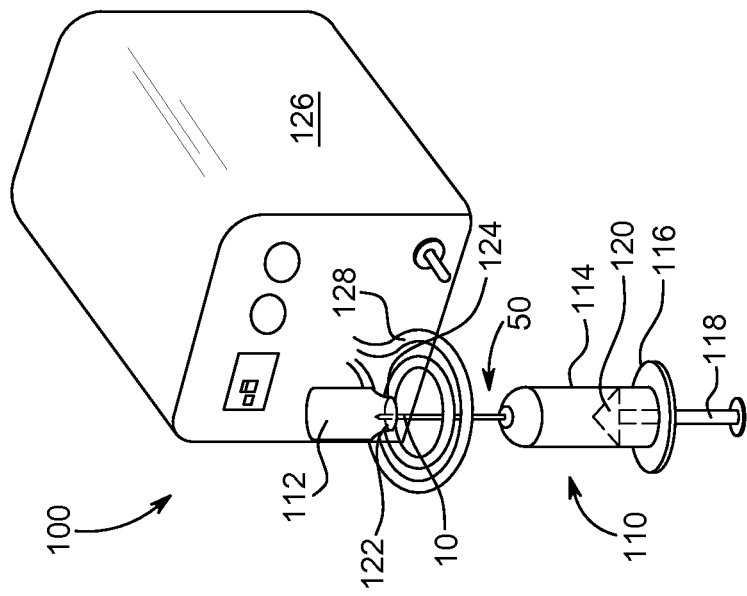
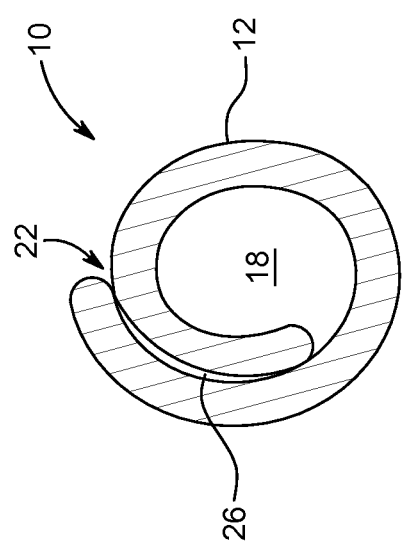

EXPANDING NEEDLE DEVICE AND METHOD OF EXPANSION FOR THE TRANSFER OF FLUIDS

BACKGROUND OF THE DISCLOSURE

Field of the Disclosure

The present disclosure is related to the medical field and, more particularly, to an expanding needle and expanding needle device for use with fluid delivery and transfer systems.

Description of Related Art

Needles and spikes are used in medical procedures and techniques, such as for drug preparation, drug delivery, and collection of fluid samples. A needle generally includes a tubular body having a tip or point sharpened on a distal end thereof. Needles for medical use are often formed from medical grade metal materials, such as stainless steel, by a tube drawing process. The needle may be connected to a retaining structure, such as a needle hub, which is connected to a fluid source or fluid conduit.

Fluid flow rate through a needle is limited by a combination of the pressure exerted on the fluid, such as by a plunger or stopper of a syringe, and the inner diameter of the needle. Accordingly, wider needles provide a faster flow rate. However, wider needles may cause increased pain when inserted through a patient's skin and may cause increased bruising at the injection site.

In addition, in fluid transfer applications, wider needles core septa and seals, preventing the septa or seal from properly resealing once the needle is removed. More specifically, during a fluid transfer activity, a technician, nurse, pharmacist, or other trained professional pushes a needle attached to the syringe through a piercable septa covering an opening of a medical vial to establish fluid communication between the vial and syringe barrel. Once fluid communication between the barrel and vial interior is established, fluid can be drawn into the syringe, to prepare a syringe for injection, or expelled into the vial, such as during drug reconstitution. The fluid flow rate through the needle is dependent on the cross sectional area of the needle and the pressure developed within the syringe barrel. However, the cross sectional area of the syringe is necessarily limited since a needle having a large cross sectional area would core the piercable septa when inserted therethrough. A septa that has been cored may not seal correctly once the needle is removed therefrom leading to fluid leakage or contamination. Accordingly, a needle intended to pierce a resilient septa generally is not larger than 16 gauge.

More recently, automated drug compounding systems have been developed. Such automated systems include electro-mechanical components for performing one or more of the following functions: inserting a needle into a fluid container, such as a vial or bag; for drawing fluid from the container; and/or for expelling fluid into the container from a fluid source, such as a syringe barrel. Operational speed for such automated systems is limited by the fluid flow rate through the needle. Accordingly, operational speed for such systems is related to a cross sectional area of the needle.

Systems and devices have been developed for increasing fluid flow rate between containers through a needle. For example, transfer devices for safe fluid transfer of chemotherapy agents are known. Such systems or devices increase the flow of makeup air into the vial to assist in drawing fluid from the vial. However, such systems are most concerned with operator safety, namely preventing an operator or patient from being exposed to air or fluid from within the interior of the vial. Accordingly, such systems often do not substantially increase flow rate through the needle. In addition, such chemotherapy agent transfer systems are complex requiring means, such as an inflatable balloon or collapsible chamber, for providing airflow to or from the vial or container. Finally, such systems are most concerned with providing makeup air for the vial and, accordingly, may not increase flow rate or operating speed when fluid is expelled from a fluid source, such as a syringe, into the vial.

Expandable tubular bodies, which may expand to increase fluid flow rate are known in other fields. For example, stents are expandable tubular bodies formed from a metal or polymer mesh material that expand when exposed to heat. A stent is inserted through a catheter into the vasculature of a patient while in a contracted state. Once the stent reaches a desired location, the stent is expanded to provide structural support for a vein and to ensure proper fluid flow therethrough. U.S. Pat. No. 4,969,890 to Sugita et al. discloses an exemplary stent formed from a shape memory alloy tubular piece that includes a rolled Ni—Ti sheet that radially expands when heat is applied thereto.

Guide wire assemblies may be used for providing vascular access for insertion of a catheter and stent. For example, U.S. Pat. No. 8,663,168 to Chin et al. discloses a flexible needle formed from nitinol hypodermic tubing and designed so that the needle will bend as it is advanced through a patient's vasculature. Similarly, U.S. Pat. No. 7,803,142 to Longson et al. is directed to a needle that includes a sheath having defined slots therein. The needle may be formed from a shape memory alloy, such as nitinol, so that an interior structure can spread the sheath outward. The sheath expands to allow a guide wire assembly and catheter to pass through the expanded needle lumen. However, these expandable tubular bodies are not used for fluid delivery or fluid transfer applications. Particularly, the expandable portions of these tubular bodies include slots or openings and, as such, cannot be used for fluid transfer applications. In addition, the nitinol alloy material used for such flexible needle assemblies is chosen for its large strain capability, rather than for its shape memory properties.

SUMMARY OF THE DISCLOSURE

For at least the foregoing reasons, it is desirable to develop an expanding needle and expanding needle device that can be inserted into skin tissue or other objects in a narrow form and then, after insertion, expanded to increase the flow rate of fluid through the needle. Such a needle reduces pain and bruising during fluid injections. Such an expandable needle also reduces time required for fluid transfer between a syringe and medical vial and, as a result, increases operating speed for an automated drug compounding system. It is also desirable to design a syringe and vial assembly that does not core a piercable septa and, as such, avoids fluid leak or contamination. The expanding needle and expanding needle device disclosed in detail herein are configured to address these issues.

The present disclosure generally relates to an expanding needle and expanding needle device. The expanding needle is used in fluid transfer and fluid delivery applications. According to one aspect, an expanding needle is provided that includes, for example, a tubular body having a proximal end, a needle-tipped distal end, and a lumen extending therebetween. The expanding needle also includes a longitudinal seam formed on the tubular body. The tubular body is configured to uncurl radially, along the longitudinal seam, thereby transitioning the tubular body from a contracted state to an expanded state to increase an inner diameter of the lumen.

In certain embodiments, the tubular body is formed by, for example, a continuous flexible sheet rolled in a lengthwise direction. In that case, the longitudinal seam is defined by a portion of a side of the flexible sheet overlapping an opposing side of the flexible sheet. The tubular body may include a shape memory material. Furthermore, in certain embodiments, the tubular body is narrower than 16 gauge when in the contracted state and wider than 14 gauge in the expanded state. In other embodiments, the tubular body is formed from a tubular needle structure having a longitudinal slot extending at least partially therethrough.

In certain embodiments, the needle-tipped distal end of the tubular body includes a piercing or intravenous needle tip. Optionally, the piercing or intravenous needle tip is positioned on an opposite portion of the distal end of the tubular body from the longitudinal seam. In another embodiment, the longitudinal seam defines at least a portion of a venting lumen, which is separate from the lumen of the tubular body. In addition, the needle may include a flange extending radially from the proximal end of the tubular body.

According to another aspect, an expanding needle device is provided that includes an expanding needle. The expanding needle includes, for example, a tubular body and a longitudinal seam formed on the tubular body. The tubular body includes a proximal end, a needle-tipped distal end, and a lumen extending therebetween. The expanding needle device also includes a needle hub supporting at least a portion of the proximal end of the tubular body. The tubular body is configured to uncurl radially thereby transitioning the tubular body from a contracted state to an expanded state to increase an inner diameter of the lumen.

In certain embodiments, the distal end of the tubular body comprises a piercing or intravenous needle tip. Optionally, the piercing or intravenous needle tip is positioned on an opposite portion of the distal end of the tubular body from the longitudinal seam. In addition, the longitudinal seam defines at least a portion of a venting lumen, the venting lumen being separate from the lumen of the tubular body. The tubular body of the expanding needle device may be formed from a shape memory material. In that case, the tubular body may be configured to transition from the contracted state to the expanded state when exposed to heat.

In certain embodiments, the proximal end of the tubular body may include a flange seated against a portion of the needle hub. Optionally, the portion of the hub that contacts the flange biases the expanding needle in a distal direction toward a distal end of the hub. Additionally, the portion of the hub that contacts the flange may include a lubricious pad. Further still, the needle hub may include an expandable annular seal disposed about the tubular body of the expanding needle. The annular seal forms a seal between the expanding needle and an interior of the needle hub.

According to another aspect, a method of increasing an inner diameter of an expanding needle is provided. The expanding needle includes, for example, a tubular body and a longitudinal seam formed on the tubular body. The tubular body includes a proximal end, a needle-tipped distal end, and a lumen extending therebetween. The method includes applying heat to the tubular body such that the tubular body uncurls radially thereby transitioning the tubular body from a contracted state to an expanded state to increase an inner diameter of the lumen.

According to another aspect, a fluid transfer system is provided that includes a fluid transfer assembly for transferring fluid between a first container and a second container. The fluid transfer assembly includes the first container in fluid connection with a lumen of an expanding needle. The expanding needle includes, for example, a continuous flexible sheet rolled in a lengthwise direction to form a tubular body. Alternatively, the tubular body may be formed from a tubular needle structure having a longitudinal slot extending at least partially therethrough. The tubular body has a proximal end, a distal end, and the lumen extending therebetween. The needle also includes a longitudinal seam formed on the tubular body such that a portion of a side of the flexible sheet overlaps an opposing side of the sheet. The flexible sheet is configured to uncurl radially thereby transitioning the tubular body from a contracted state to an expanded state, such that an area of overlap of the seam is reduced or eliminated and an inner diameter of the lumen is increased.

In certain embodiments, the second container includes an opening covered by a piercable septum configured to be pierced by the expanding needle. In certain embodiments, the heater is configured to expose the expanding needle to heat. The system is configured such that when the piercable septum is pierced by the expanding needle, fluid communication between the first container and the second container is established through the lumen of the expanding needle. When the expanding needle is exposed to heat from the heater, the tubular body of the expanding needle transitions from the contracted state to the expanded state.

Further details and advantages of the various embodiments described in detail herein will become clear upon reviewing the following detailed description of the various embodiments in conjunction with the accompanying drawing figures.

BRIEF DESCRIPTION OF THE DRAWINGS

FIG. 4 is a longitudinal cross sectional view of another embodiment of an expanding needle.

FIG. 8 is a schematic drawing of a fluid transfer system including the expanding needle of FIG. 1.

DESCRIPTION OF THE PREFERRED EMBODIMENTS

Figure 1:
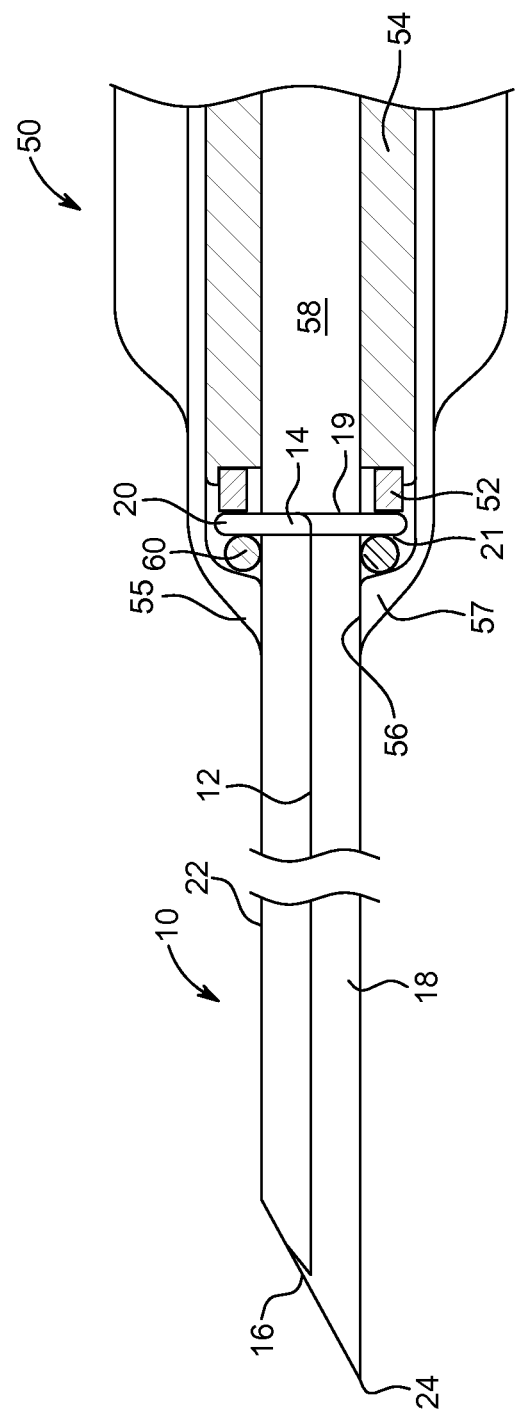
FIG. 1 is a partial cross sectional view of an embodiment of an expanding needle connected to a needle hub.
Figure 3:
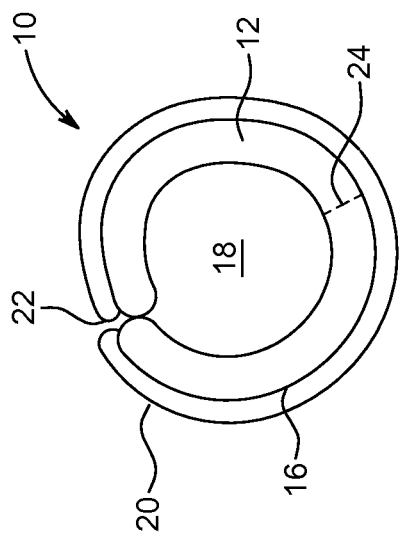
FIG. 3 is a distal view of the needle of FIG. 1, in an expanded state.
Figure 2:
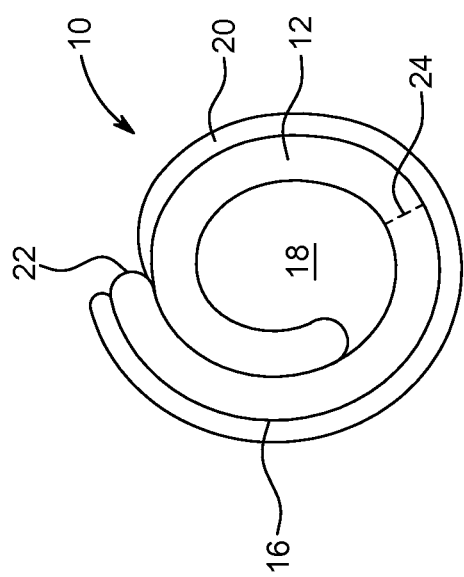
FIG. 2 is a distal view of the needle of FIG. 1, in a contracted state.

The illustrations generally show preferred and non-limiting embodiments of the systems and methods of the present disclosure. While the descriptions present various embodiments of the devices, it should not be interpreted in any way as limiting the disclosure. Furthermore, modifications, concepts, and applications of the disclosure's embodiments are to be interpreted by those skilled in the art as being encompassed, but not limited to, the illustrations and descriptions herein.

Further, for purposes of the description hereinafter, the terms "end", "upper", "lower", "right", "left", "vertical", "horizontal", "top", "bottom", "lateral", "longitudinal" and derivatives thereof shall relate to the disclosure as it is oriented in the drawing figures. The term "proximal" refers to the direction toward the portion of the syringe or device that is actuated or acted on by a user. The term "distal" refers to a direction away from the portion of the device or syringe that is acted on by a user. However, it is to be understood that the disclosure may assume various alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

With reference to the figures, an expanding needle 10 capable of transitioning from a contracted state to an expanded state is provided. The needle 10 may be used for fluid delivery and sample collection and, accordingly, is capable of piercing skin and subcutaneous tissue to obtain vascular access. The needle 10 may also be inserted through a piercable septa of a medical container, such as a medical vial or intravenous (IV) bag, while in a contracted state to reduce or prevent coring of the septa. For example, the needle 10 could be used for drawing fluid out of an IV bag, so that the space vacated by the withdrawn fluid can be replaced with some other medicinal or therapeutic agent. The piercable septa may be formed from any flexible resilient material, such as natural rubber, synthetic rubber, or silicone. Once inserted into a vein or through the septa, the expanding needle 10 may be transitioned to an expanded state to permit an increased fluid flow rate through the needle 10. Transitioning the needle 10 from the contracted state to the expanded state causes the cross sectional area of the needle 10 and the inner diameter of the needle 10 to increase. In one specific embodiment, the needle 10 may be a 16 gauge needle or narrower in the contracted state and may be a 14 gauge needle or wider in the expanded state.

In a non-limiting embodiment and with specific reference to FIGS. 1-4, the expanding needle 10 is formed from a continuous flexible sheet rolled in a lengthwise direction to form a tubular body 12. The tubular body 12 has a proximal end 14 (shown in FIG. 1), a distal end 16, and a lumen 18 extending therebetween. Optionally, a connecting structure or seating structure extends from the proximal end 14 of the tubular body 12. The connecting structure may be a flange 20, having a proximal surface 19 and distal surface 21, configured to engage or connect with a retaining structure, such as a needle hub 50 (shown in FIG. 1), for connecting the expanding needle 10 to a fluid container or fluid transfer device, such as a syringe barrel, auto-injector, fluid containing cartridge, catheter, infusion pump, flexible tubing, or catheter. The needle 10 and needle hub 50 may also be connected to a fluid pump, such as an infusion pump, by tubing or a catheter so that the needle 10 can be used for substantially continuous or periodic drug delivery.

When the continuous flexible sheet is rolled, a portion of one side of the flexible sheet overlaps the other side of the sheet to form a longitudinal seam 22 extending the length of the tubular body 12. The flexible sheet is configured to uncurl radially when exposed to an activating condition, thereby transitioning the tubular body 12 from the contracted state to the expanded state.

In another embodiment, rather than being formed from a flexible sheet rolled to form a tubular body 12, the tubular body 12 may be formed from a pre-manufactured tubular member. The tubular member may be formed by a tube drawing process suitable for creating a narrow extended metal or metal alloy tube. In that case, the longitudinal seem 22 is formed by cutting a longitudinal slit through the tubular member to form the tubular body 12. The tubular body 12 may then be contracted causing one side of the longitudinal slit to overlap the other side of the slit. Once in the contracted state, the tubular body 12 may be set or annealed by applying heat thereto, which causes the tubular body 12 to remain in its contracted state after the heat is removed. After annealing, the needle 10 remains in its contracted state until heat or another activating condition is applied, which causes the needle 10 to transition to its expanded state.

At least a portion of the continuous flexible sheet or tubular member may be formed from a shape memory alloy, such as nickel titanium (e.g., nitinol). As used herein, shape memory refers to a material that changes shape when exposed to a particular activating condition. The activating condition may be a temperature change (e.g., exposure to heat/cold). For example, the needle 10 may expand when exposed to body heat of a patient, such as when the needle 10 is inserted into the patient's skin. The needle 10 may also be heated by an external heat source. Other exemplary activating conditions include exposure to various wavelengths of energy (e.g., radio frequencies or infrared radiation), sound frequencies, electric charge, or other activating conditions as are known in the art. The flexible sheet may also be formed from other shape memory materials, such as various polymer materials, within the scope of the present disclosure. In certain embodiments, the entire flexible sheet is formed from the shape memory material. In other embodiments, the sheet or tubular member may include shape memory portions connected with portions formed from other non-shape memory materials.

The expanding needle 10 may be a single-use needle. In that case, the needle 10 need only be capable of a single transition, namely the transition from the contracted state to the expanded state. A single-use needle 10 does not need to return to its original shape after the activating condition is removed. Once the expanded single-use needle 10 is removed from the patient or piercable septa, it may be discarded. Alternatively, the expanding needle 10 may be a multi-use needle. In that case, the shape memory material is capable of transitioning from the contracted state to the expanded state when exposed to the activating condition. After the activating condition is removed, the multi-use needle 10 contracts. It is noted that shape memory materials generally do not return all the way to their original position when an activating condition is removed. Accordingly, removing the activating condition generally does not cause the needle 10 to contract all the way to its original size and shape. Instead, to work as a multi-use needle, the needle 10 need only to contract a sufficient amount so that it can be reused for a desired application. In addition, in certain embodiments, the pierced rubber septa or stopper may exert a biasing force on the needle 10 assisting it to return to a more contracted position.

With continued reference to FIGS. 1-4, the distal end 16 of the needle 10 may include a tip 24 or point. The tip 24 may be a piercing tip suitable for piercing a rubber septa or stopper. When used for intravascular fluid delivery or sample collection, the tip is an intravascular tip capable of piercing skin and subcutaneous tissue for insertion into a patient's vein. The tip 24 or point may be formed on one side of the distal end 16 of the tubular body 12. The tip 24 or point is preferably sufficiently sharp and structurally stable for insertion through a piercable septa. In one embodiment, the tip 24 may be positioned on the opposite side of the distal end 16 of the tubular body 12 from the longitudinal seam 22.

With specific reference to FIG. 4, in one embodiment, the longitudinal seam 22 defines at least a portion of a second lumen. The second lumen, which is referred to hereinafter as a venting lumen 26, is separate from the lumen 18 extending through the tubular body 12 of the expanding needle 10. The venting lumen 26 vents air from or to the container or vial as fluid is drawn into or removed from the vial. For example, when fluid is expelled from the syringe and into the vial, air is permitted to escape from the vial through the venting lumen 26 and into ambient atmosphere. Similarly, when fluid is drawn from the vial and into the syringe, ambient air, referred to as makeup air, is drawn through the venting lumen 26 and into the vial. The makeup air equalizes pressure and prevents formation of a negative pressure or vacuum that would make drawing fluid out of the vial more difficult.

Figure 5A:
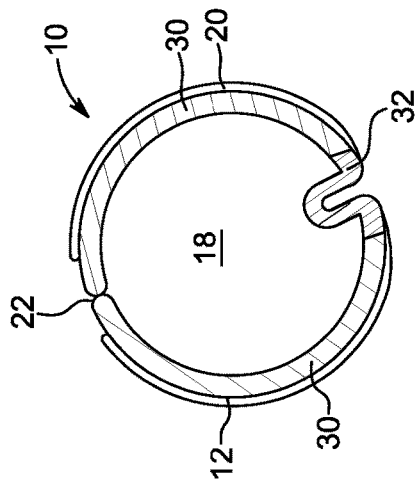
FIG. 5A is a cross sectional view of another embodiment of an expanding needle, in a contracted state.
Figure 5B:
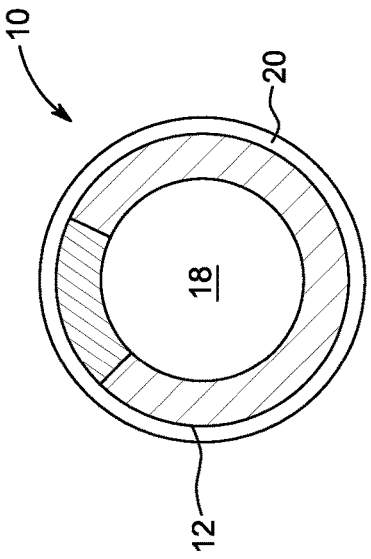
FIG. 5B is a cross sectional view of the needle of FIG. 5A, in an expanded state.

With reference to FIGS. 5A and 5B, another embodiment of an expanding needle 10 having a central lumen 18 is illustrated. The needle 10 is substantially similar to previously described needles formed by rolling a flexible sheet to form a tubular body 12 and having a radial flange 20 extending from a proximal end thereof. However, in the embodiment of FIGS. 5A and 5B, the flexible sheet is formed from at least two distinct portions having distinct material properties. The first portion, referred to as a shape-memory portion 32, may extend longitudinally through the sheet to form a hinge or joint. The shape memory portion 32 is formed from a shape memory material, such as nitinol. The shape memory portion 32 is positioned substantially in the middle of the sheet, such that when the sheet is rolled, the shape memory portion 32 is opposite from the longitudinal seam 22. The remainder of the flexible sheet, referred to as a non-shape memory portion 30, may be formed from a flexible, but non-shape memory material, such as a metal or polymer material. As shown in FIG. 5A, when the needle 10 is in the contracted state, the sides of the flexible sheet overlap at the longitudinal seam 22, with the shape memory portion 32 being wider compared to the state of the shape memory portion 32 when the needle 10 is in expanded state shown in FIG. 5B. As shown in FIG. 5B, when an activating condition is applied to the needle 10, the shape memory portion 32 becomes narrower causing the tubular body 12 to uncurl along the seam 22, thereby transitioning the needle 10 to its expanded state.

Figure 6A:
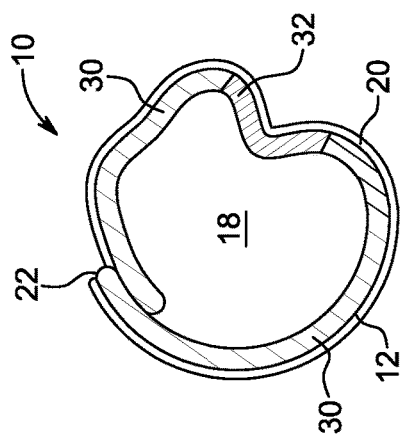
FIG. 6A is a cross sectional view of another embodiment of an expanding needle, in a contracted state.
Figure 6B:
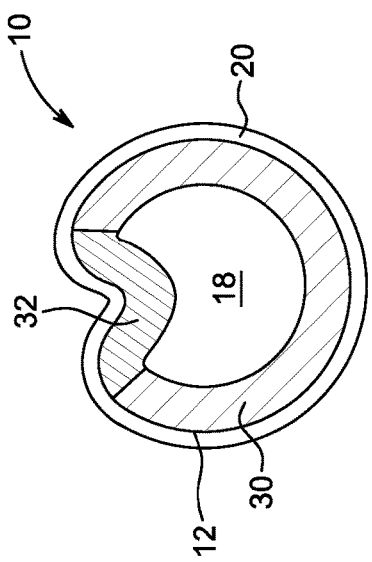
FIG. 6B is a cross sectional view of the needle of FIG. 6A, in an expanded state.

With reference to FIGS. 6A and 6B, in another embodiment, the expanding needle 10 includes a shape memory portion 32 joined to a partially annular non-shape memory portion 30. As in previously described embodiments, the expanding needle 10 is formed from a tubular body 12 that defines a central lumen 18. A radial flange 20 extends from a proximal end of the tubular body 12. As shown in FIG. 6A, in the contracted state, the shape memory portion 32 is deflected inward toward the central lumen 18. As a result of the deflection, the cross sectional area of the central lumen 18 is reduced. As shown in FIG. 6B, in the expanded state, the shape memory portion 32 is biased radially outward giving the lumen 18 a circular cross section. It is noted that in the embodiment of FIGS. 6A and 6B, the non-shape memory portion 30 is not required to move or uncurl as the tubular body 12 transitions between the contracted and expanded states. Accordingly, the non-shape memory portion may be formed from a stiff or rigid material, such as stainless steel.

Figure 7:
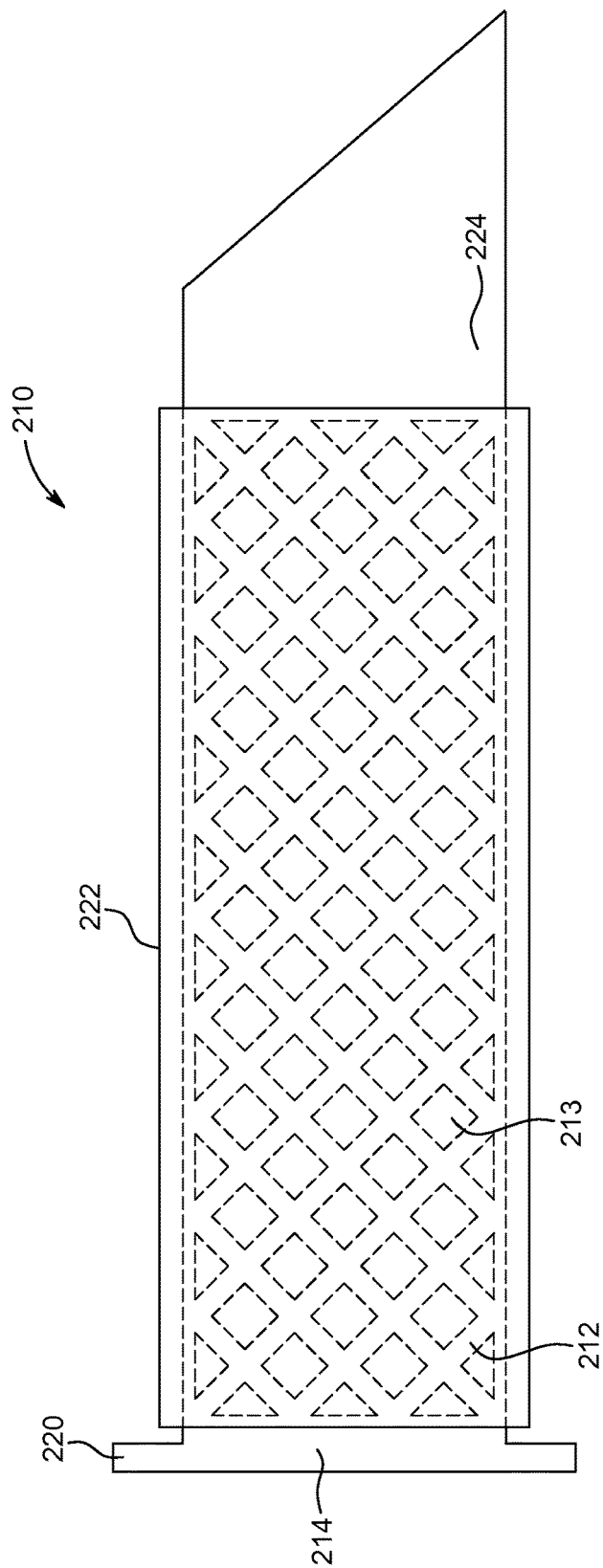
FIG. 7 is a schematic drawing of a side view of another embodiment of an expanding needle.

With reference to FIG. 7, in another embodiment, an expanding needle 210 may take the form of a stent. For example, rather than being formed from a single continuous sheet of flexible material or a slotted tube, the expanding needle 210 may include an expandable mesh 212 formed from a shape memory material. The mesh 212 may be formed from shape memory threads woven together to form a suitable pattern. The mesh 212 may also be formed by cutting openings 213 or pores into a tubular body 212 to create the mesh 212 pattern. As shown in FIG. 7, the mesh 212 is covered by a flexible cover 222 capable of expanding along with the mesh 212. Desirably, the cover 222 includes a waterproof, fluid-tight, or hydrophobic material that prevents fluid from passing through the cover 222 and permits good fluid flow through the needle 210. For example, the cover 222 may be formed from rolled stainless steel. Upon exposure to an activating condition, the mesh 212 expands. The threads or openings 213 may reposition or change shape causing the needle 210 to transition from its contracted state to an expanded state. For example, while transitioning from the contracted state to the expanded state, portions of the threads may straighten or unwind, thereby increasing the inner diameter of the stent structure. Similarly, the openings 213 may become more elongated to increase the diameter of the tubular body 212. As in the previously discussed embodiments, the needle 210 includes a tip 224 or point protruding from the distal end of the cover 222. Similarly, the needle 210 includes a connecting structure, such as a flange 220, at the proximal end 214 thereof, that protrudes from the proximal end of the cover 222. The tip 224 and flange 220 may be integrally formed with the mesh 212. Alternatively, the tip 224 and flange 220 may be connected to the mesh 212 by a fastener or adhesive. In yet another embodiment, the tip 224 and flange 220 may be part of the cover 222. In that case, the mesh tubular body 212 is inserted in or enclosed by the cover 222. The tubular body 212 provides structural support for the cover 222, flange 220, and tip 224.

Having described the structure of the expanding needle 10, an expanding needle device including a needle hub 50 that retains the expanding needle 10 will now be discussed. The hub 50 is configured to retain the needle 10 both in its contracted and expanded states and, accordingly, includes adjustable structures for this purpose. With reference again to FIG. 1, the hub 50 includes a housing 55 having an opening 56 on a distal end 57 thereof. The expanding needle 10 is seated to the needle hub 50 and extends through the opening 56. For example, the proximal surface 19 of the flange 20 may be pressed against a receiving structure, such as a lubricious pressure pad 52. The pad 52 is connected to a needle retainer 54. The needle retainer 54 is a tubular body within the housing 55. In certain embodiments, the retainer 54 biases the pad 52 and flange 20 in the distal direction toward the distal end 57 of the housing 55. A fluid conduit 58 or lumen extends through the tubular needle retainer 54. Fluid from the expanding needle 10 is transported through the conduit 58 of the needle hub 50 and to a fluid container, such as a syringe barrel (not shown), attached to the hub 50.

The hub 50 also includes a flexible seal, such as an expandable o-ring 60, positioned between the distal surface 21 of the flange 20 and an interior portion of the distal end 57 of the housing 55. The needle retainer 54 may bias the flange 20 and o-ring 60 toward the distal end 57 of the housing 55 to maintain good contact therebetween. The o-ring 60 forms a seal between the sidewall of the tubular body 12 and the opening 56 of on the housing 55, thereby preventing fluid or other materials from entering the needle hub 50 through the opening 56 when the expanding needle 10 is in the contracted state. The expandable o-ring 60 is preferably formed from a resilient flexible structure that expands in conjunction with expansion of the needle 10. For example, the o-ring 60 may be formed from rubber, silicone, or any other elastomeric material.

Having described the needle 10 and needle hub 50, a fluid transfer system 100 including the expanding needle 10 will now be discussed in detail. With reference to FIG. 8, the system 100 can be used for transferring fluid between medical containers, such as between a syringe 110 and medical vial 112. The syringe 110 includes a syringe barrel 114 having an open proximal end 116, with a plunger rod 118 extending therefrom. The plunger rod 118 is configured to drive a stopper or plunger 120 through the syringe barrel 114 to draw fluid into or expel fluid from an interior of the barrel 114. The needle hub 50 is connected to the distal end of the syringe barrel 114. An expending needle 10 is connected to the syringe barrel 114 through the needle hub 50, such that a fluid conduit is created between the syringe barrel 114 and expanding needle 10 through the needle hub 50. The expanding needle 10 is configured to be inserted into an interior of the vial 112 through a piercable septa 122 covering an opening 124 of the vial 112.

The system 100 also includes a radio frequency heater 126 having a radio frequency coil 128 extending therefrom. As shown in FIG. 8, the expanding needle 10 is placed within the radio frequency coil 128. Actuating the radio frequency heater 126 causes the coil 128 to induce heat in the expanding needle 10, thereby causing the needle 10 to transition from the contracted state to the expanded state. The coil 128 may be formed from any suitable material capable of inducing heat in the expanding needle 10. Alternatively, a radiant heat coil with sufficient resistance to produce heat for expanding the needle 10 may also be used for the same purpose. A coolant may flow through the coil to control or limit heat radiating from the coil.

In use, a technician, medical professional, or robotic device obtains the syringe 110 and medical vial 112. The user or robotic device may attach the expanding needle 10 to the syringe 110 or needle hub 50. Alternatively, in the case of certain disposable syringes, the expanding needle 10 may be connected to the syringe 110 during manufacture. In that case, the needle 10 may be covered by a cap or shield (not shown) that should be removed prior to use. Once the cap or shield is removed, the user or robotic device inserts the expanding needle 10 of the syringe 110 into the vial 112 through the septa 122. Since the expanding needle 10 is in a contracted state, the needle 10 does not core the septa 122 during insertion.

Once the needle 10 is inserted into the vial 112, the needle 10 is inserted in or placed in close proximity to the radio frequency coil 128 of the heater 126. Alternatively, the needle 10 may be placed in proximity to the coil 128 before it is inserted to the vial 112. In either case, once the needle 10 and coil 128 are correctly positioned, the heater 126 is activated and the needle 10 expands from the contracted state to the expanded state. Expansion of the needle 10 causes the inner diameter of the needle 10 to expand so that the fluid flow rate through the needle 10 increases. For single use needles, that do not contract after heat is removed, the syringe 110 and needle 10 may be removed from the heater 126 or heat source after the expansion is complete since, once expanded, the expanding needle 10 is locked in the expanded state. The user then retracts the plunger rod 118 to draw fluid from the vial 112 into the syringe barrel 114 or advances the plunger rod 118 through the syringe barrel 114 to expel fluid into the vial 112. For multi-use expanding needles 10, the user must keep the expanding needle 10 in close proximity to the heat source to prevent the needle 10 from contracting. While still in close proximity to the heat source, the user uses the plunger rod 118 to transfer fluid to or from the syringe barrel 114. Once the fluid transfer is complete, the user can turn off the heat source or move the syringe 110 and needle 10 away from the heat source allowing the expanding needle 10 to contract. A biasing or resealing force of the septa 122 may assist in contracting the needle 10. Once contracted, the user can remove the expanding needle 10 from the piercable septa 122 of the vial 112. Once the expanding needle 10 is removed, the piercable septa 122 reseals to prevent fluid from leaking from the vial 112. Alternatively, the user or robotic device may remove the needle 10 from the septa 122 prior to allowing the needle 10 to contract. Once the needle 10 is removed from the septa 122 and the heat source, the needle 10 contracts from its expended state to a contracted state.

Figure 9:
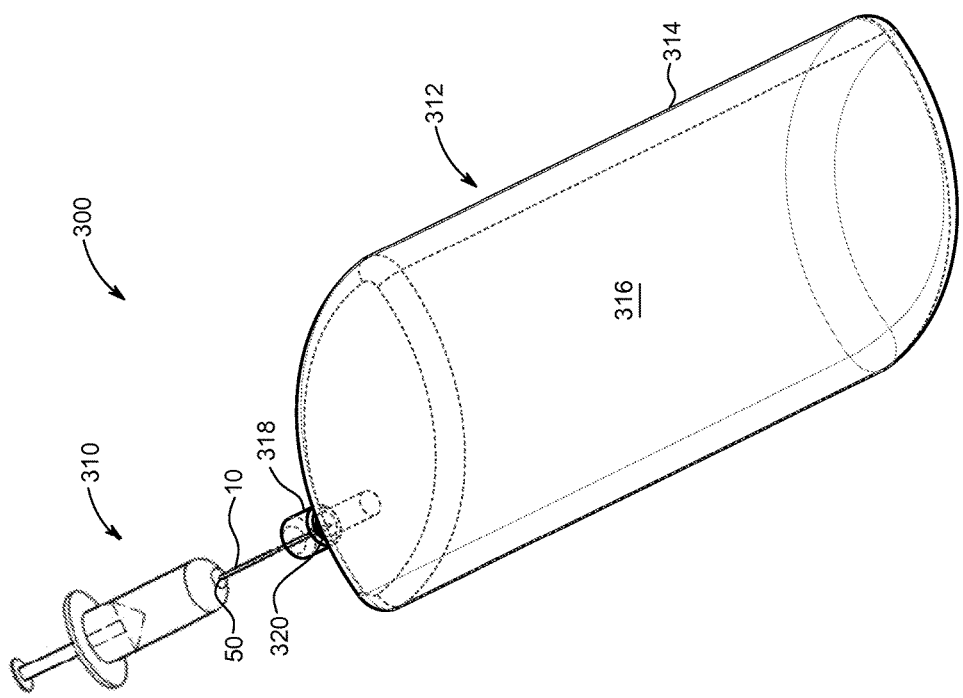
FIG. 9 is a schematic drawing of another embodiment of a fluid transfer system including the expanding needle of FIG. 1.

With reference to FIG. 9, an embodiment of a fluid delivery system 300 for transferring fluid between a syringe 310 and an IV bag 312 is illustrated. The syringe 310 is substantially similar to previously described syringes, and includes a needle hub 50 and expanding needle 10 extending from the hub 50. The IV bag 312 includes a body 314 formed from a flexible water-proof material, such as poly vinyl chloride (PVC), and defining an interior 316 configured to contain a volume of fluid. The interior 316 is accessible through a port 318 covered by a piercable septa 320. A heating element, such as a radio frequency coil, may be integrally formed with the port 318 or at a location on the bag 312 in close proximity to the port 318. Alternatively, the heating element may be positioned at any other suitable and convenient location, such as connected to the body 314 of the IV bag 312 or on a portion of the syringe 310. The syringe 310 can be used for providing fluid to and for withdrawing fluid from the interior 316 of the bag 312.

The system 300 may be used to prepare fluid in the IV bag 312 for delivery to a patient. In one embodiment, an IV bag 312 containing a fluid or solvent, such as saline solution is provided. A user inserts the expanding needle 10 into the interior 316 of the bag 312 through the piercable septa 320 to provide fluid access to the interior 316 of the bag 312. The heating element may then be activated causing the needle 10 to transition from its contracted state to its expanded state. The user then withdraws the solvent or fluid from the bag 312 to create vacant space in the IV bag 312. Once the vacant space is provided, the user then removes the needle 10 from the bag 312 and allows the piercable septa 320 to reseal. The user then inserts another expanding needle 10 connected to another syringe 310 through the septa 320 and into the interior 316 of the bag 312. The second syringe 310 may contain another type of fluid, such as a medicinal or therapeutic agent. Mixing the solvent or fluid, such as saline solution, with the therapeutic agent provides a solution suitable for delivery to the patient. Once the bag 312 is prepared, the fluid contents of the bag can be delivered to the patient, such as be connecting a catheter to the port 318 and allowing fluid to drain from the bag 312 to the patient.

While embodiments of an expanding needle, expanding needle device, and system were provided in the foregoing description, those skilled in the art may make modifications and alterations to these embodiments without departing from the scope and spirit of the disclosure. Accordingly, the foregoing description is intended to be illustrative rather than restrictive. The disclosure described hereinabove is defined by the appended claims and all changes to the disclosure that fall within the meaning and the range of equivalency of the claims are to be embraced within their scope.

The invention claimed is:

1. An expanding needle comprising:
  a tubular body comprising a proximal end, a distal end comprising a needle tip, and a lumen extending therebetween for expelling fluid from and/or drawing fluid into the tubular body and through the lumen; and
  a longitudinal seam formed in the tubular body,
  wherein the tubular body is biased to uncurl radially along the longitudinal seam upon exposure to an activating condition, thereby transitioning the tubular body from a contracted state to an expanded state to increase an inner diameter of the lumen, thereby increasing fluid flow rate through the lumen,
  wherein the tubular body comprises a shape memory material, and
  wherein the activating condition comprises applying at least one of heat, infrared radiation, sound frequencies, electric charge, and radiofrequency signals to the tubular body.

2. The expanding needle of claim 1, wherein the tubular body comprises a flexible sheet rolled in a lengthwise direction, and wherein the longitudinal seam is defined by a portion of a side of the flexible sheet overlapping an opposing side of the flexible sheet.

3. The expanding needle of claim 1, wherein an area of overlap of the longitudinal seam is reduced or eliminated when the tubular body transitions from the contracted state to the expanded state.

4. The expanding needle of claim 1, wherein the needle tip of the tubular body comprises a piercing or intravenous needle tip.

5. The expanding needle of claim 1, wherein the tubular body is narrower than 16 gauge when in the contracted state and wider than 14 gauge in the expanded state.

6. The expanding needle of claim 1, wherein the proximal end of the tubular body comprises a flange extending radially therefrom.

7. The expanding needle of claim 1, further comprising a cover surrounding the tubular body, wherein the tubular body comprises an expandable mesh enclosed by the cover.

8. The expanding needle of claim 1, wherein a cross-sectional area of the tubular body in the contracted state is less than a cross-sectional area of the tubular body in the expanded state, along an entire length of the tubular body.

9. The expanding needle of claim 1, wherein the cross-sectional area of the tubular body increases by the same amount along the entire length of the tubular body during transition of the tubular body from the contracted state to the expanded state.

10. The expanding needle of claim 1, wherein the longitudinal seam defines at least a portion of a venting lumen extending between the proximal end and the distal end of the tubular body when the tubular body is in the contracted state, the venting lumen being separate from the lumen of the tubular body.

11. An expanding needle device, comprising:
  an expanding needle comprising:
    a tubular body comprising a proximal end, a distal end comprising a needle tip, and a lumen extending therebetween for expelling fluid from and/or drawing fluid into the tubular body and through the lumen; and
    a longitudinal seam formed in the tubular body; and
  a needle hub supporting at least a portion of the proximal end of the tubular body,
  wherein the tubular body is biased to uncurl radially along the longitudinal seam upon exposure to an activating condition, thereby transitioning the tubular body from a contracted state to an expanded state to increase an inner diameter of the lumen, thereby increasing fluid flow rate through the lumen,
  wherein the tubular body comprises a shape memory material, and
  wherein the activating condition comprises applying at least one of heat, infrared radiation, sound frequencies, electric charge, and radiofrequency signals to the tubular body.

12. The expanding needle device of claim 11, wherein the needle tip of the tubular body comprises a piercing or intravenous needle tip.

13. The expanding needle device of claim 11, wherein the proximal end of the tubular body comprises a flange seated against a portion of the needle hub.

14. The expanding needle device of claim 13, wherein the portion of the hub that contacts the flange biases the expanding needle in a distal direction toward a distal end of the hub.

15. The expanding needle device of claim 14, wherein the portion of the hub that contacts the flange comprises a lubricious pad.

16. The expanding needle device of claim 15, wherein the needle hub comprises an expandable annular seal disposed about the tubular body of the expanding needle that forms a seal between the expanding needle and an interior of the needle hub.

17. A syringe comprising:
  a syringe barrel defining an interior volume; and
  an expanding needle connected to the syringe barrel, the expanding needle comprising:
    a tubular body comprising a proximal end, a distal end comprising a needle tip, and a lumen extending therebetween, the lumen being in fluid communication with and configured to draw fluid into and/or expel fluid from the interior of the syringe barrel;
    a longitudinal seam formed in the tubular body; and
    a plunger disposed in the syringe barrel, wherein advancing the plunger distally through the syringe barrel expels fluid from the syringe barrel and through the lumen of the expanding needle, and wherein retracting the plunger draws fluid into the syringe barrel,
  wherein the tubular body is biased to uncurl radially along the longitudinal seam upon exposure to an activating condition, thereby transitioning the tubular body from a contracted state to an expanded state to increase an inner diameter of the lumen, thereby increasing fluid flow rate through the lumen.

18. The syringe of claim 17, wherein the tubular body of the expanding needle comprises a flexible sheet rolled in a lengthwise direction, and wherein the longitudinal seam is defined by a portion of a side of the flexible sheet overlapping an opposing side of the flexible sheet.

19. The syringe of claim 17, wherein the needle tip of the tubular body comprises a piercing or intravenous needle tip.

20. The syringe of claim 17, wherein the tubular body comprises a shape memory material, and wherein the activating condition comprises applying at least one of heat, infrared radiation, sound frequencies, electric charge, and radiofrequency signals to the tubular body.

21. The syringe of claim 17, wherein the longitudinal seam of the expanding needle defines at least a portion of a venting lumen extending between the proximal end and the distal end of the tubular body when the tubular body is in the contracted state, the venting lumen being separate from the lumen of the tubular body.

22. The syringe of claim 17, further comprising a needle hub connected to the syringe barrel and supporting the expanding needle, wherein the proximal end of the tubular body of the expanding needle comprises a flange seated against a portion of the needle hub.

23. The expanding needle device of claim 22, wherein the portion of the hub that contacts the flange comprises a lubricious pad.

\* \* \* \* \*

UNITED STATES PATENT AND TRADEMARK OFFICE
CERTIFICATE OF CORRECTION

PATENT NO. : 10,279,124 B2
APPLICATION NO. : 14/602711
DATED : May 7, 2019
INVENTOR(S) : Robert Eckert It is certified that error appears in the above-identified patent and that said Letters Patent is hereby corrected as shown below:

In the Claims

Column 13, Line 21, Claim 23, delete "expanding needle device" and insert -- syringe --

Signed and Sealed this
Ninth Day of July, 2019

Andrei Iancu
*Director of the United States Patent and Trademark Office*